(12) United States Patent
Slavazza et al.

(10) Patent No.: US 11,571,677 B2
(45) Date of Patent: Feb. 7, 2023

(54) PEPTIDE SYNTHESIS INSTRUMENTATION

(71) Applicant: CSBio Instrumentation Co., Menlo Park, CA (US)

(72) Inventors: Dario Slavazza, Fremont, CA (US); Yoheng Chang, Foster City, CA (US); David Lippoth, Grand Junction, CO (US)

(73) Assignee: CSBIO INSTRUMENTATION CO., Menlo Park, CA (US)

( * ) Notice: Subject to any disclaimer, the term of this patent is extended or adjusted under 35 U.S.C. 154(b) by 49 days.

(21) Appl. No.: 16/949,399

(22) Filed: Oct. 28, 2020

(65) Prior Publication Data
US 2022/0126259 A1  Apr. 28, 2022

(51) Int. Cl.
*B01J 19/24* (2006.01)
*C07K 1/04* (2006.01)
*B01D 29/03* (2006.01)
*B01D 29/56* (2006.01)
*B01J 19/00* (2006.01)

(52) U.S. Cl.
CPC ............ *B01J 19/242* (2013.01); *B01D 29/03* (2013.01); *B01D 29/56* (2013.01); *B01J 19/0046* (2013.01); *C07K 1/045* (2013.01); *B01J 2219/0004* (2013.01); *B01J 2219/00286* (2013.01); *B01J 2219/00346* (2013.01); *B01J 2219/00423* (2013.01); *B01J 2219/00495* (2013.01); *B01J 2219/00725* (2013.01)

(58) Field of Classification Search
None
See application file for complete search history.

(56) References Cited

U.S. PATENT DOCUMENTS

| 3,531,258 | A | * | 9/1970 | Merrifield | C07K 1/045 422/116 |
| 4,517,338 | A | * | 5/1985 | Urdea | C07H 21/00 435/317.1 |
| 4,668,476 | A | * | 5/1987 | Bridgham | C07K 1/045 422/111 |
| 4,748,002 | A | * | 5/1988 | Neimark | B01J 19/0046 422/131 |

(Continued)

FOREIGN PATENT DOCUMENTS

| DE | 29921606 U1 | * | 4/2001 | ......... B01J 19/0046 |
| FR | 2554820 A | * | 5/1985 | ......... B01J 19/0046 |
| WO | WO-2004069401 A2 | * | 8/2004 | ......... B01F 13/0255 |

*Primary Examiner* — Jennifer A Leung
(74) *Attorney, Agent, or Firm* — Innovation Capital Law Group, LLP; Vic Lin

(57) ABSTRACT

A peptide synthesis instrument can be used for small scale peptide synthesis. The instrument can include several unique features, including a compression style reaction vessel permitting quick setup of the reaction vessel, a double reaction vessel system permitting efficient mixing without loss of solvent or solvent-to-resin contact, gravity-fed heated reservoirs establishing a fixed volume for delivery to the reaction vessel, fume-free solvent addition permitting solvent addition to fixed bottles, and an improved amino acid manifold assembly which reduces the number of components and increases the ease of use of the instrument. Each of these features improve upon the current state of the art in solid phase automated peptide synthesizers.

19 Claims, 19 Drawing Sheets

(56) References Cited

U.S. PATENT DOCUMENTS

| | | | | |
|---|---|---|---|---|
| 5,147,608 | A | * | 9/1992 | Hudson .................. C07K 1/045 |
| | | | | 422/63 |
| 5,203,368 | A | * | 4/1993 | Barstow .................... B01J 4/02 |
| | | | | 137/240 |
| 5,624,638 | A | * | 4/1997 | Negrotti ............. G09B 19/0069 |
| | | | | 206/229 |
| 5,762,881 | A | * | 6/1998 | Harness ............... B01J 19/0046 |
| | | | | 422/138 |

* cited by examiner

PEPTIDE SYNTHESIS INSTRUMENTATION

BACKGROUND OF THE INVENTION

1. Field of the Invention

Embodiments of the invention relate generally to automated chemical synthesis. More particularly, embodiments of the invention relate to an automated peptide synthesizer for small scale peptide synthesis.

2. Description of Prior Art and Related Information

The following background information may present examples of specific aspects of the prior art (e.g., without limitation, approaches, facts, or common wisdom) that, while expected to be helpful to further educate the reader as to additional aspects of the prior art, is not to be construed as limiting the present invention, or any embodiments thereof, to anything stated or implied therein or inferred thereupon.

Peptide synthesis refers to the production of peptides, compounds where multiple amino acids are linked via peptide bonds. Peptides are chemically synthesized by the condensation reaction of the carboxyl group of one amino acid to the amino group of another. Chemical peptide synthesis most commonly starts at the carboxyl end of the peptide (C-terminus), and proceeds toward the amino-terminus (N-terminus).

The chemical synthesis of peptides can be carried out using classical solution-phase techniques, as well as solid-phase methods. One established method for the production of synthetic peptides in the lab is known as solid-phase peptide synthesis which allows the rapid assembly of a peptide chain through successive reactions of amino acid derivatives on an insoluble porous support. Since the peptide under construction remains covalently attached to the support throughout the synthesis, excess reagents and side products can be removed by washing and filtration.

There is a need, however, for improvements to known automated peptide synthesizers, including those addressed by the present invention.

SUMMARY OF THE INVENTION

Embodiments of the present invention provide a reaction vessel for a chemical synthesis device comprising a hollow tubular body; a first filter disposed at a first end of the hollow tubular body; a cap, such as a threaded cap, fitting on a second end of the hollow tubular body; a second filter disposed in the cap, where an interior region is defined between the first filter and the second filter when the cap is attached on the second end of the hollow tubular body; a first tapered fitting on the first end of the hollow tubular body providing fluid communication from outside the reaction vessel to the interior region; and a second tapered fitting on the cap providing fluid communication from outside the reaction vessel to the interior region.

Embodiments of the present invention further provide a chemical synthesis device comprising a reaction vessel; a lower connector configured to provide sealed engagement to a lower tapered fitting of a reaction vessel; an upper connector configured to provide sealed engagement to an upper tapered fitting of the reaction vessel; a knob attached to the upper connector; and an upper connector path formed in a housing of the chemical synthesis device, the upper connector path permitting movement of the knob and upper connector upward to disconnect the upper connector from the upper tapered fitting, and downward to a reaction vessel connection position where the upper connector engages with the upper tapered fitting of the reaction vessel.

In some embodiments, the lower connector is movable downward against a resilient force, such as a force provided by one or more springs.

In some embodiments, the chemical synthesis device further comprises a force application mechanism to provide a downward force to the knob upper connector, urging the upper connector to the reaction vessel connection position. This force application mechanism can be a weight disposed inside the housing.

In some embodiments, the upper connector path includes a vertical component, permitting the upper connector to engage to and disengage from the upper tapered end, and a horizontal component, permitting the upper connector to be maintained in a non-engagement position with the upper connector disengaged from the upper tapered end.

In some embodiments, the chemical synthesis device further comprises a heating element configured to provide heat to one or more reaction vessel holding arms.

Embodiments of the present invention also provide a double reaction vessel system for a chemical synthesis device comprising a first reaction chamber having fittings at an upper end and a lower end thereof; a second chamber fluidly connected at its lower end to the upper end of the first reaction chamber; a waste connection at an upper end of the second chamber; a first inert gas connection at the upper end of the second chamber, the first inert gas connection operable to provide an inert gas flow through the second chamber, from the upper end to the lower end, and into the first reaction chamber; and a second inert gas connection operable to provide an inert gas into the first reaction chamber via the lower end thereof.

In some embodiments, the double reaction vessel system further comprises a solution flow connection at a lower end of the first chamber operable to provide a solvent or a solution into the first reaction chamber.

In some embodiments, the double reaction vessel system further comprises a solvent flow connection at the upper end of the second chamber providing a rinse solvent flow through the second chamber and the first chamber.

In some embodiments, the double reaction vessel system further comprises a waste flow connection at the lower end of the first chamber operable to provide the rinse solvent to a waste container.

In some embodiments, the double reaction vessel system further comprises one or more three-way valves operable to adjust a flow through at least one of the first reaction chamber or the second chamber.

These and other features, aspects and advantages of the present invention will become better understood with reference to the following drawings, description and claims.

BRIEF DESCRIPTION OF THE DRAWINGS

Some embodiments of the present invention are illustrated as an example and are not limited by the figures of the accompanying drawings, in which like references may indicate similar elements.

Figure 1:
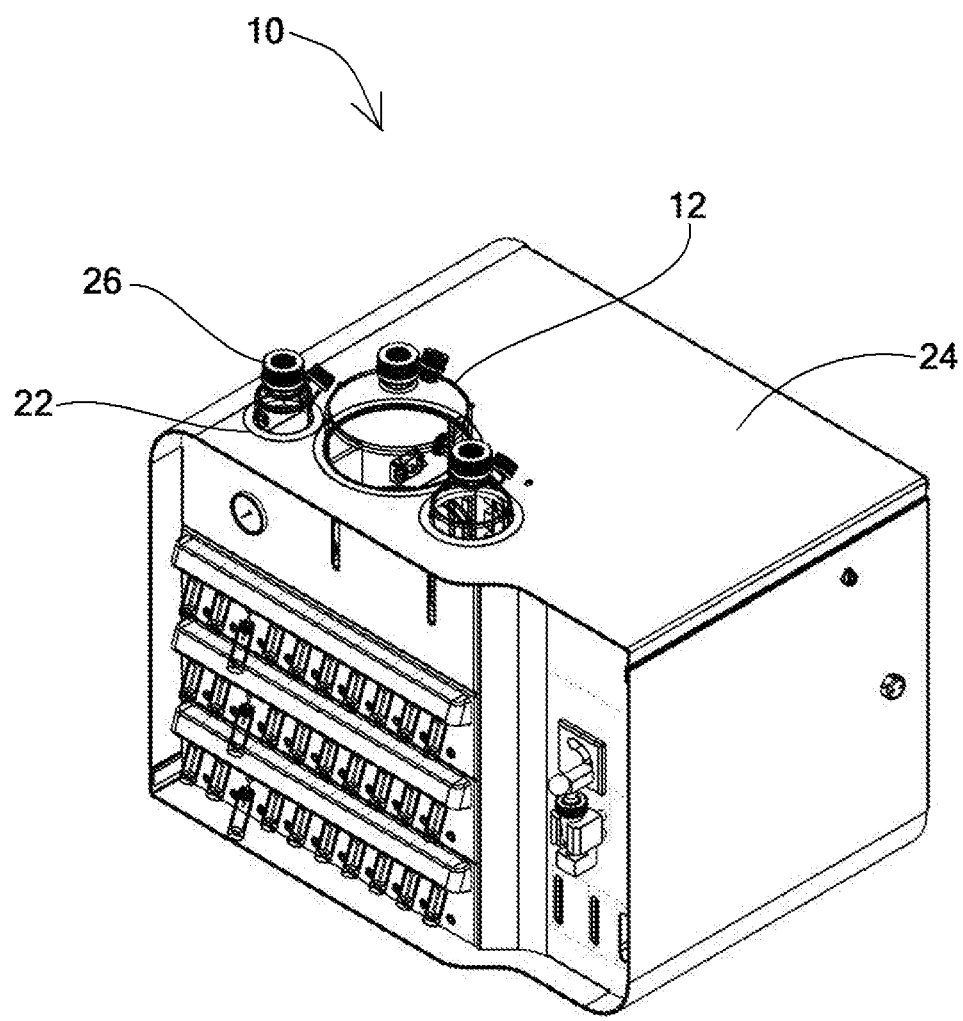
FIG. 1 illustrates a perspective view of a chemical synthesis instrument according to an exemplary embodiment of the present invention.

Unless otherwise indicated illustrations in the figures are not necessarily drawn to scale.

The invention and its various embodiments can now be better understood by turning to the following detailed description wherein illustrated embodiments are described. It is to be expressly understood that the illustrated embodiments are set forth as examples and not by way of limitations on the invention as ultimately defined in the claims.

DETAILED DESCRIPTION OF THE PREFERRED EMBODIMENTS AND BEST MODE OF INVENTION

The terminology used herein is for the purpose of describing particular embodiments only and is not intended to be limiting of the invention. As used herein, the term "and/or" includes any and all combinations of one or more of the associated listed items. As used herein, the singular forms "a," "an," and "the" are intended to include the plural forms as well as the singular forms, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

Unless otherwise defined, all terms (including technical and scientific terms) used herein have the same meaning as commonly understood by one having ordinary skill in the art to which this invention belongs. It will be further understood that terms, such as those defined in commonly used dictionaries, should be interpreted as having a meaning that is consistent with their meaning in the context of the relevant art and the present disclosure and will not be interpreted in an idealized or overly formal sense unless expressly so defined herein.

In describing the invention, it will be understood that a number of techniques and steps are disclosed. Each of these has individual benefit and each can also be used in conjunction with one or more, or in some cases all, of the other disclosed techniques. Accordingly, for the sake of clarity, this description will refrain from repeating every possible combination of the individual steps in an unnecessary fashion. Nevertheless, the specification and claims should be read with the understanding that such combinations are entirely within the scope of the invention and the claims.

In the following description, for purposes of explanation, numerous specific details are set forth in order to provide a thorough understanding of the present invention. It will be evident, however, to one skilled in the art that the present invention may be practiced without these specific details.

The present disclosure is to be considered as an exemplification of the invention and is not intended to limit the invention to the specific embodiments illustrated by the figures or description below.

As is well known to those skilled in the art, many careful considerations and compromises typically must be made when designing for the optimal configuration of a commercial implementation of any system, and in particular, the embodiments of the present invention. A commercial implementation in accordance with the spirit and teachings of the present invention may be configured according to the needs of the particular application, whereby any aspect(s), feature(s), function(s), result(s), component(s), approach(es), or step(s) of the teachings related to any described embodiment of the present invention may be suitably omitted, included, adapted, mixed and matched, or improved and/or optimized by those skilled in the art, using their average skills and known techniques, to achieve the desired implementation that addresses the needs of the particular application.

Broadly, embodiments of the present invention provide a peptide synthesis instrument that can be used for small scale peptide synthesis. The instrument can include several unique features, including a compression style reaction vessel permitting quick setup of the reaction vessel, a double reaction vessel system permitting efficient mixing without loss of solvent or solvent-to-resin contact, gravity-fed heated reservoirs establishing a fixed volume for delivery to the reaction vessel, fume-free solvent addition permitting solvent addition to fixed bottles, and an improved amino acid manifold assembly which reduces the number of components and increases the ease of use of the instrument. Each of these features improve upon the current state of the art in solid phase automated peptide synthesizers.

Figure 2:
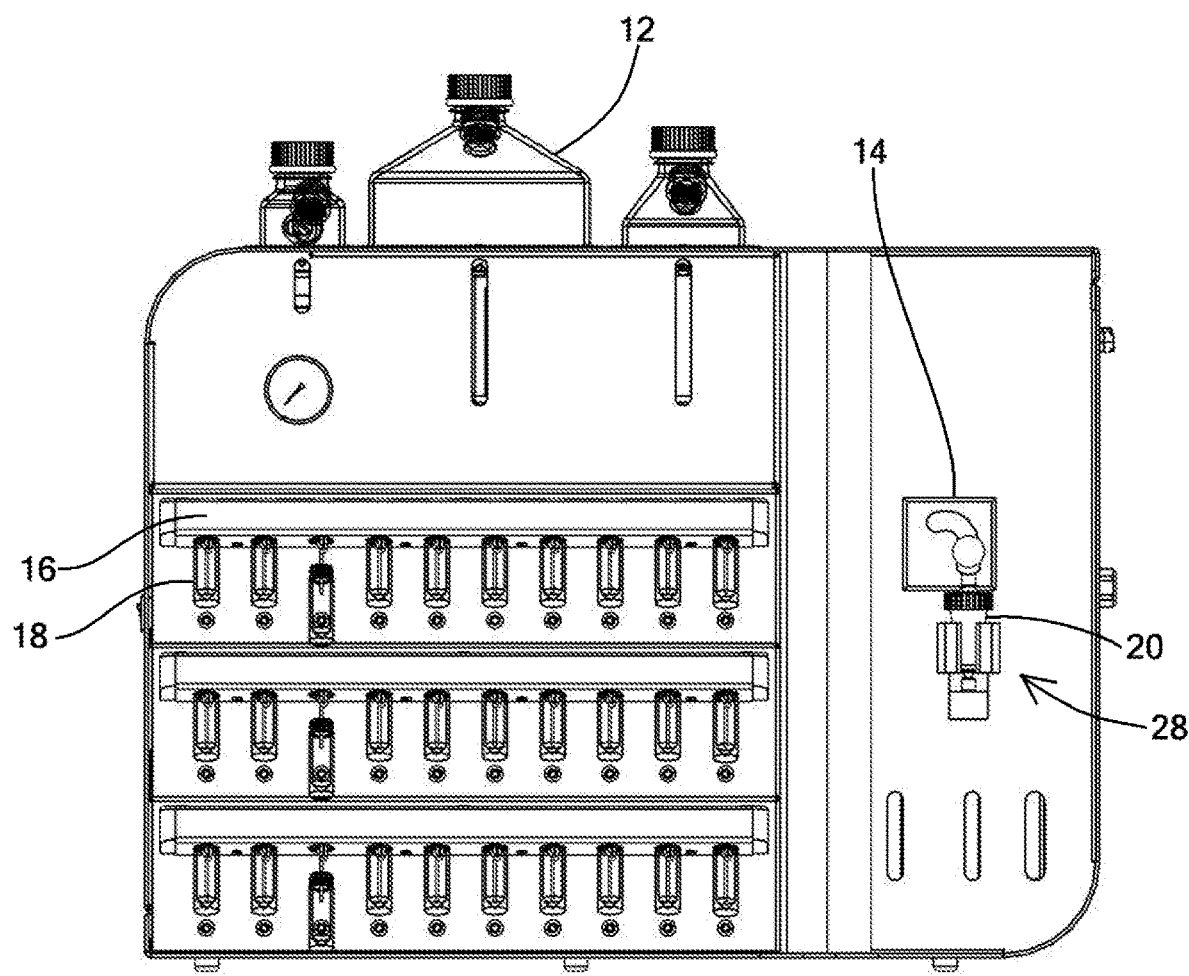
FIG. 2 illustrates a front view of the chemical synthesis instrument of FIG. 1.
Figure 3:
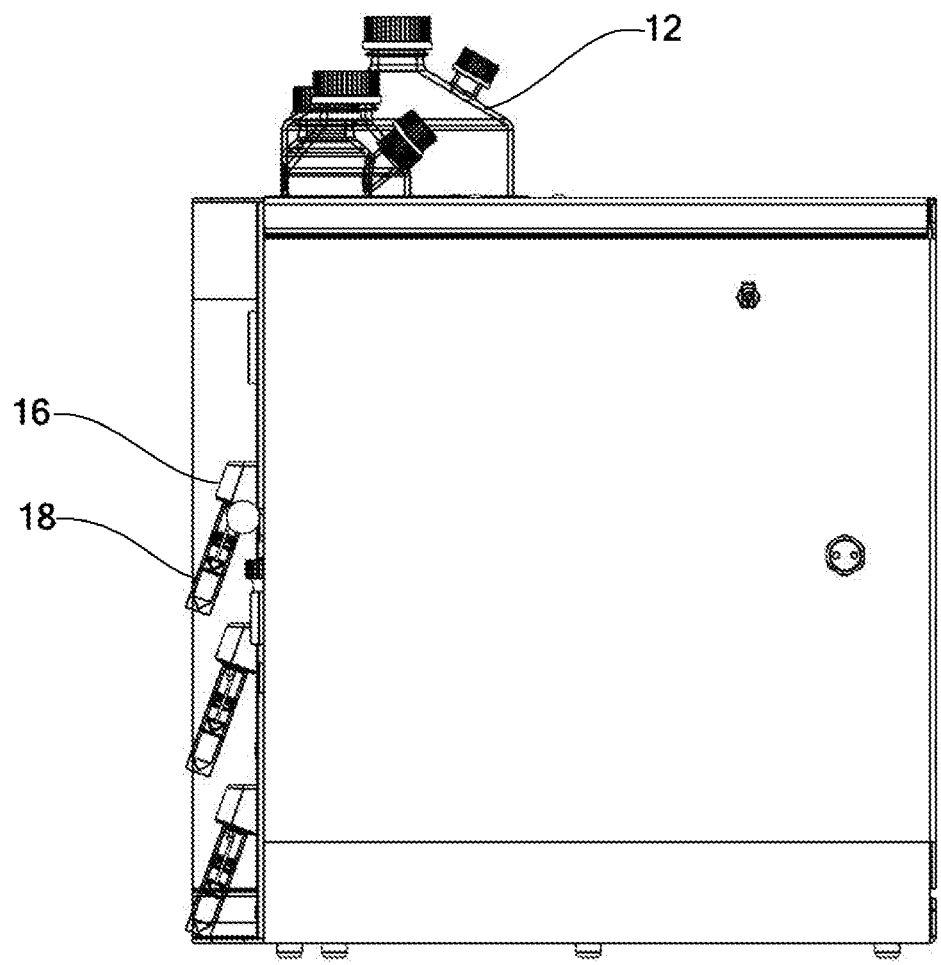
FIG. 3 illustrates a side view of the chemical synthesis instrument of FIG. 1.

Referring to FIGS. 1 through 3, a peptide synthesis instrument 10, also referred to as instrument 10, can include a plurality of solvent bottles 12 at least partially disposed in a housing 24 of the instrument 10. In some embodiments, as described in greater detail below, at least one of the solvent bottles 12 can be fixed to the housing and can be provided with a gasket 22 that retains the solvent bottles 12 in place. Such gaskets 22 prevent rotation of the solvent bottles 12, thus permitting the bottle caps 26 to be removed or applied with a single hand, for example.

The instrument 10 can include a reaction vessel attachment location 28, where a reaction vessel 20 can be attached. A mechanism 14, as described in greater detail below, can be used for compression connection of the reaction vessel 20 to the instrument 10. As described in greater detail below, the mechanism 14 can be a dual action compression mechanism for attachment of the reaction vessel 20.

Figure 4:
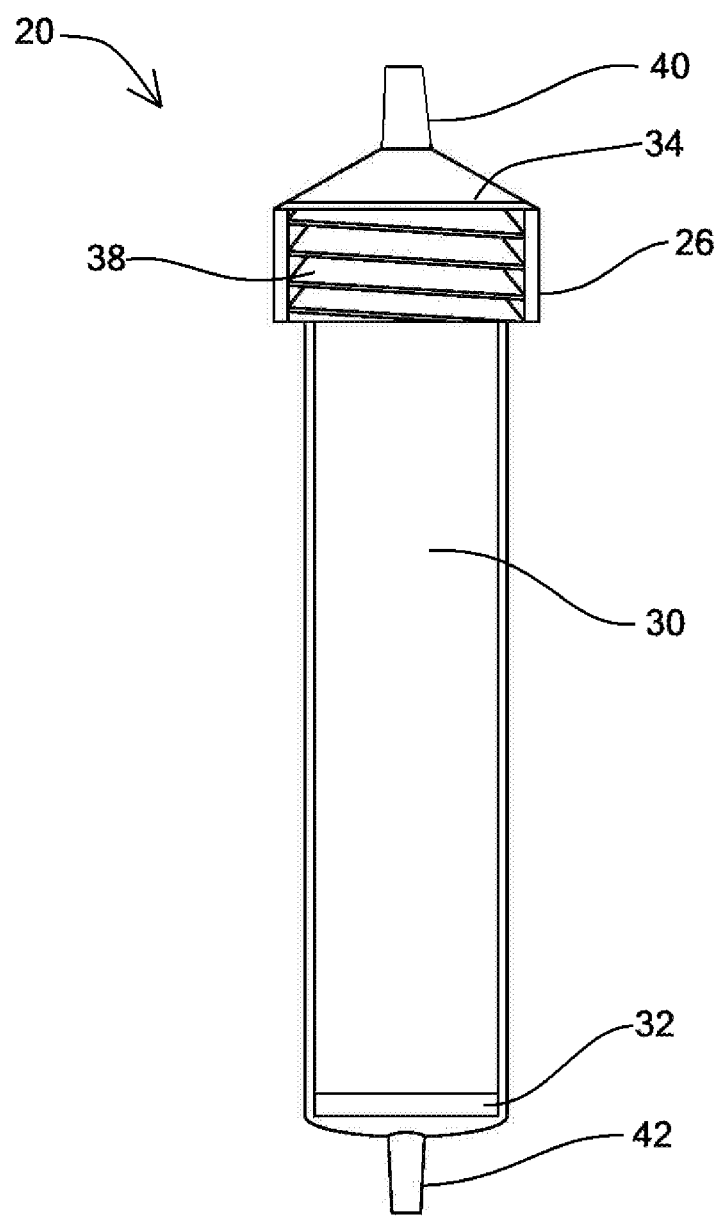
FIG. 4 illustrates a reaction vessel usable in the chemical synthesis instrument of FIG. 1.

Referring now to FIG. 4, a reaction vessel 20 can include an interior region 30 with a filter 32 at a bottom portion thereof. The filter 32 can be designed to prevent solid phase material, such as resin, from moving therethrough, while allowing solvent or solubilized reagent to flow therethrough. A cap 36, such as a threaded cap, may removably fit, via threads 38, on an upper end of the reaction vessel 20. The cap 36 may fit on the upper end of the reaction vessel 20 in other manners as well, such as a friction fit, a snap fit, a luer lock-type connection, or the like. The cap 36 can include a filter 34 therein, similar in design and function as filter 32. When the cap 36 is removed, a user has access to the interior region 30. When the cap is applied on the reaction vessel 20, an upper tapered end 40 of the cap 36 provides fluid communication, through the filter 34, to the interior region 30. A lower tapered end 42 can provide fluid communication, through the filter 32, to the interior region 30.

Conventional methods for connecting a reaction vessel to a peptide synthesis instrument includes threaded ends. Embodiments of the present invention provide tapered ends 40, 42 to allow for quick setup of the reaction vessel 20 into the instrument 10, as described in greater detail below.

Referring now to FIGS. 5 through 9, detailed views illustration the compression mechanism 14 is shown. The reaction vessel 20, with its tapered ends 40, 42 (see FIG. 4) can be compression fitted into a lower connector 52 and an upper connector 50. Arms 44 can secure the reaction vessel 20 in position. The arms 42 can be heated by the instrument 10, via known methods, to heat the reaction vessel 20, as needed.

Figure 8:
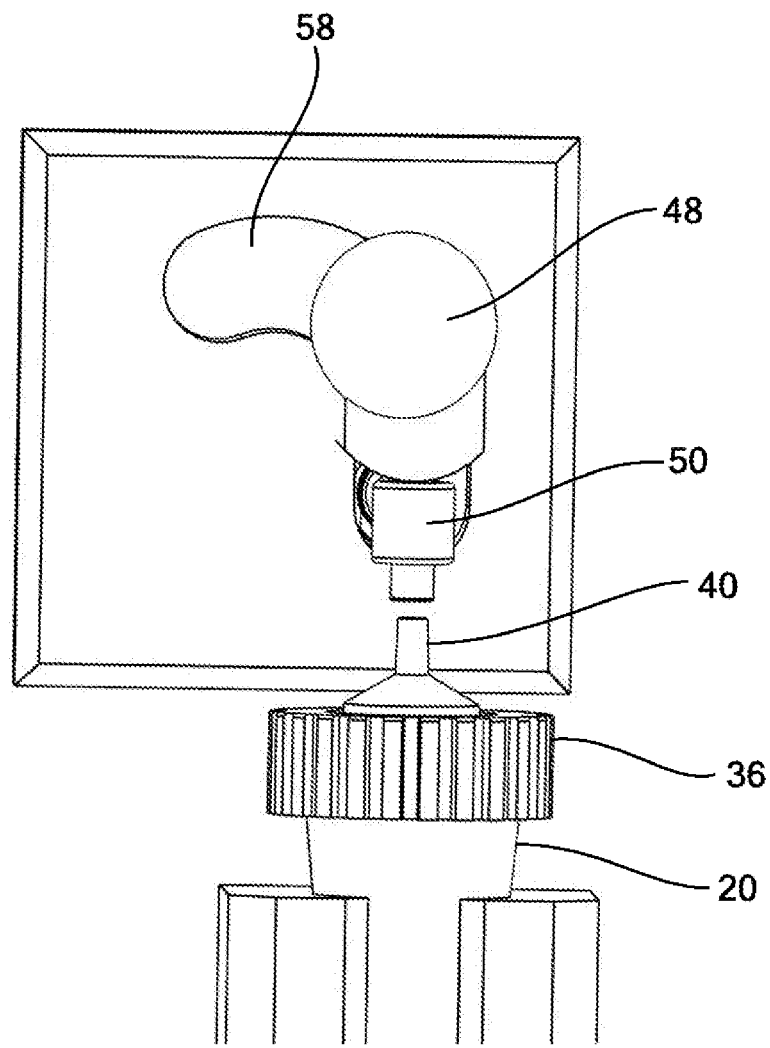
FIG. 8 illustrates a detailed front view of an upper connection of the double action compression reaction vessel connection mechanism of FIG. 5.

A knob 48 can be provided to lift the upper connector 50 off of the upper tapered end 40 of the cap 36, as best illustrated in FIG. 8. A weight 56 may be provided, typically behind the housing 24, to provide a downward force to the upper connector 50 into the upper tapered end 40. Of course, other methods of providing a downward force may be used, such as springs, bands, pneumatic pressure, or the like.

Figure 5:
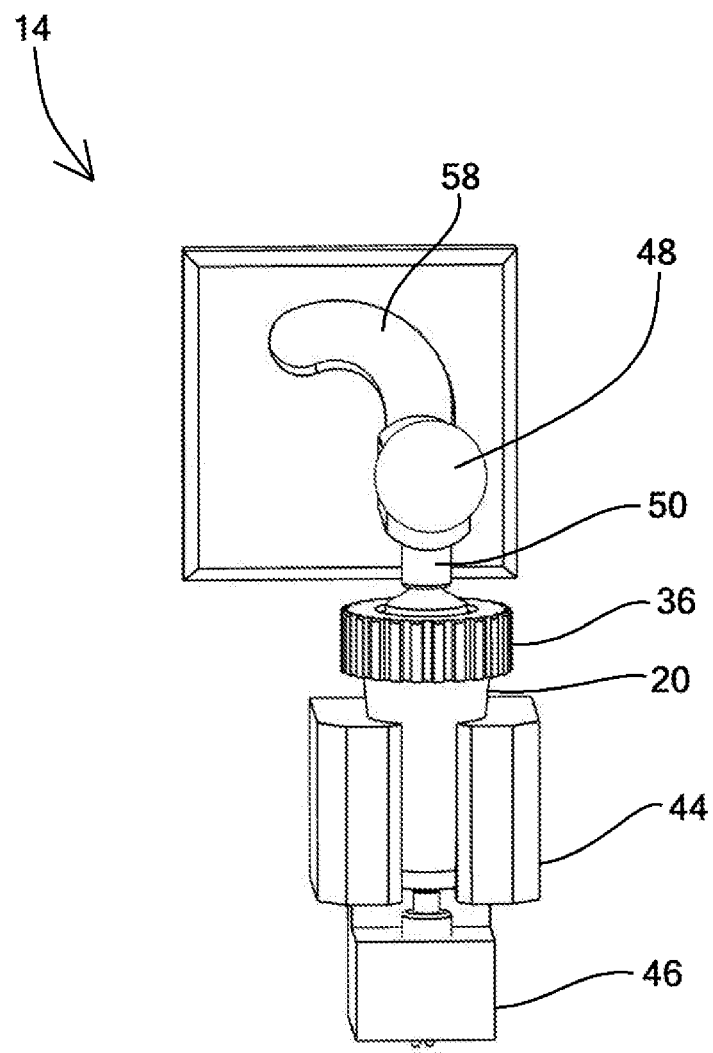
FIG. 5 illustrates a detailed view of a double action compression reaction vessel connection mechanism usable on the chemical synthesis instrument of FIG. 1.

The knob 48 may be first moved in a generally upward direction, as shown in FIG. 8, to separate the upper connector 50 from the upper tapered end 40. The knob 48 may then move generally horizontally and then slightly downward along a track 58. The slightly downward trajectory may be used to retain the knob 48 (and the connected upper connector 50) from inadvertently moving back into the engaged configuration (as shown in FIG. 5, for example).

Figure 6:
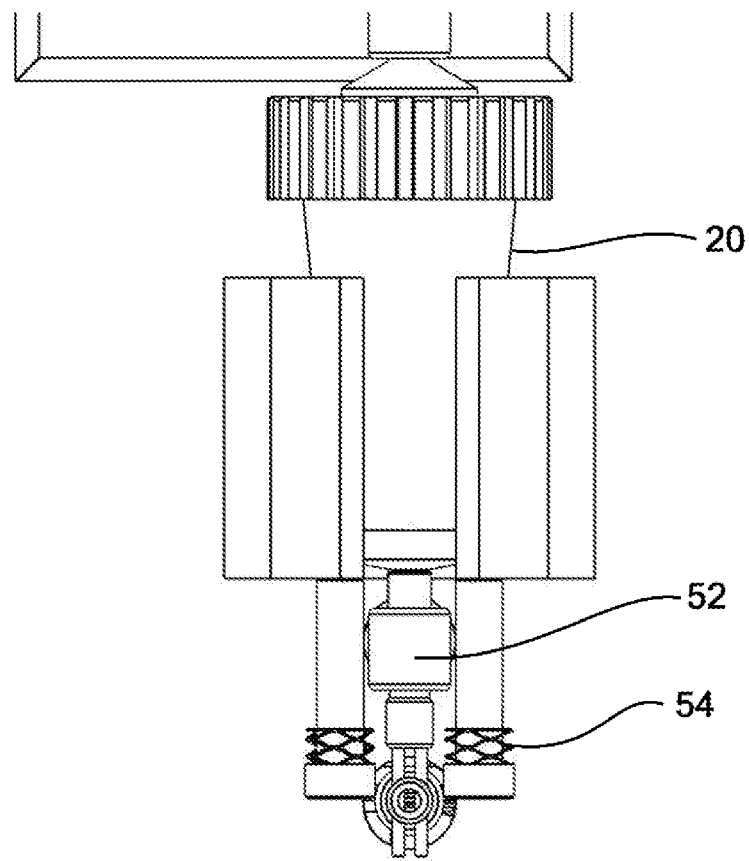
FIG. 6 illustrates a detailed view of the double action compression reaction vessel connection mechanism of FIG. 5 with a base portion removed therefrom.
Figure 7:
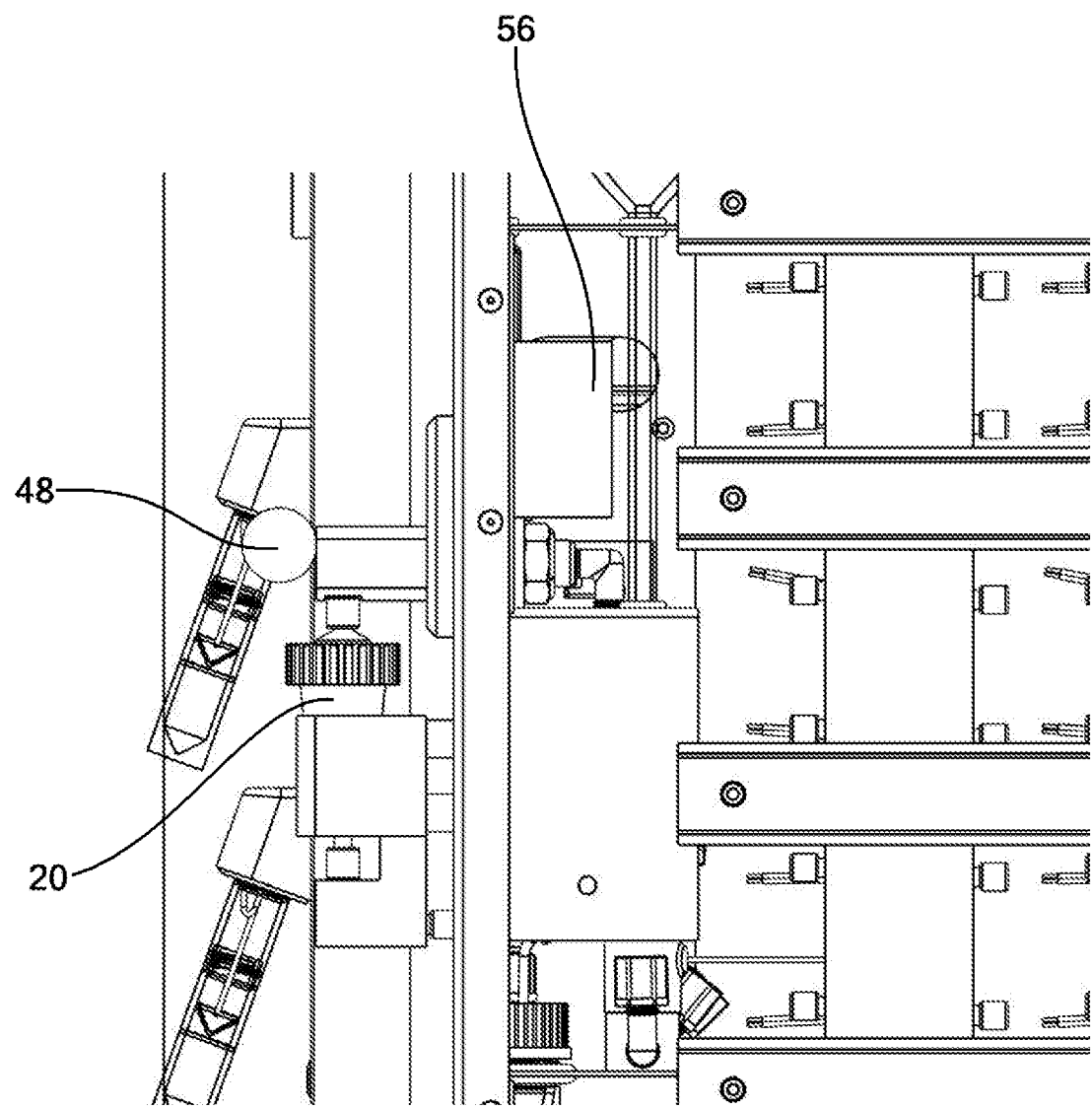
FIG. 7 illustrates detailed side view of the chemical synthesis instrument of FIG. 1.

FIG. 6 illustrates a reaction vessel foot 46 removed to illustrate the lower connector 52. Springs 54, or other similar resiliently deformable means, can be used to provide an upward force on the lower connector 52, urging the lower connector 52 toward the lower tapered end 42 of the reaction vessel 20. The combined loaded forces of the weight 56 and the springs 54 can ensure even pressure at both ends to make the appropriate seals between the upper connector 50 and the upper tapered end 40 as well as between the lower connector 52 and the lower tapered end 42.

Figure 10:
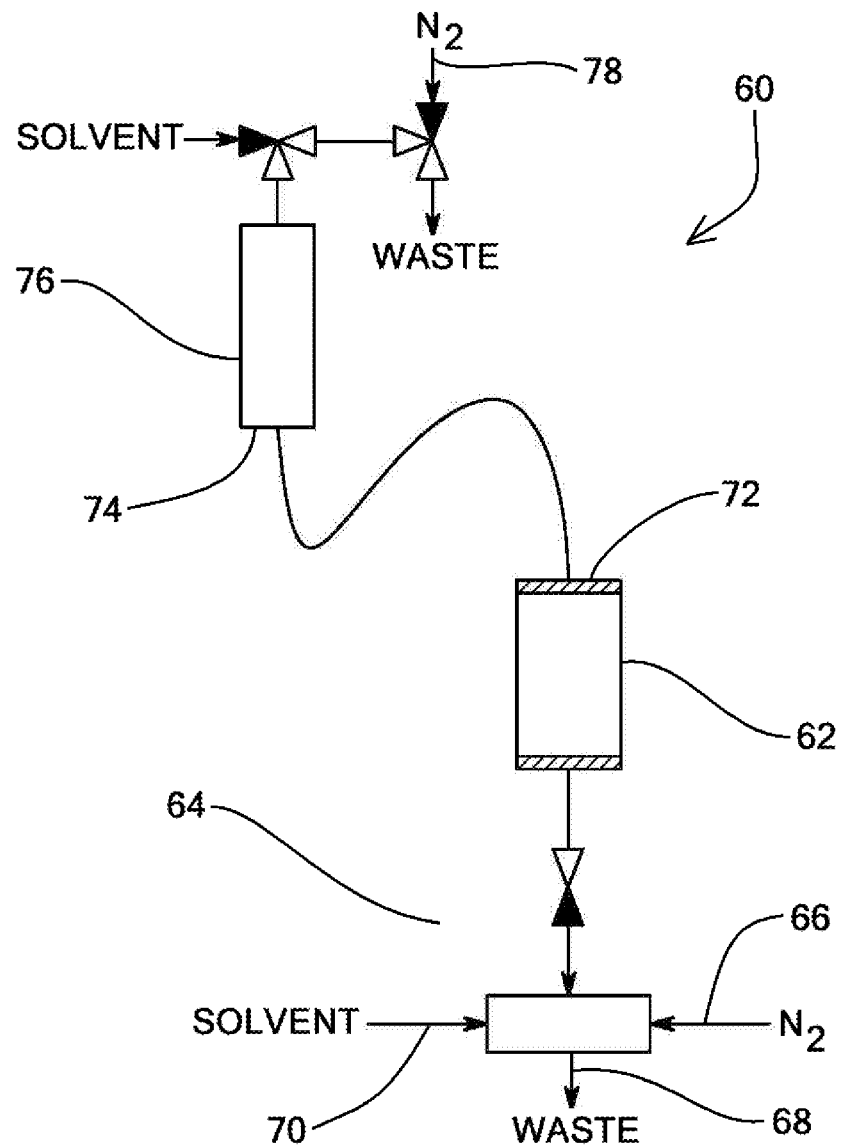
FIG. 10 illustrates a schematic representation of a double reaction vessel system usable in the chemical synthesis instrument of FIG. 1.
Figure 11:
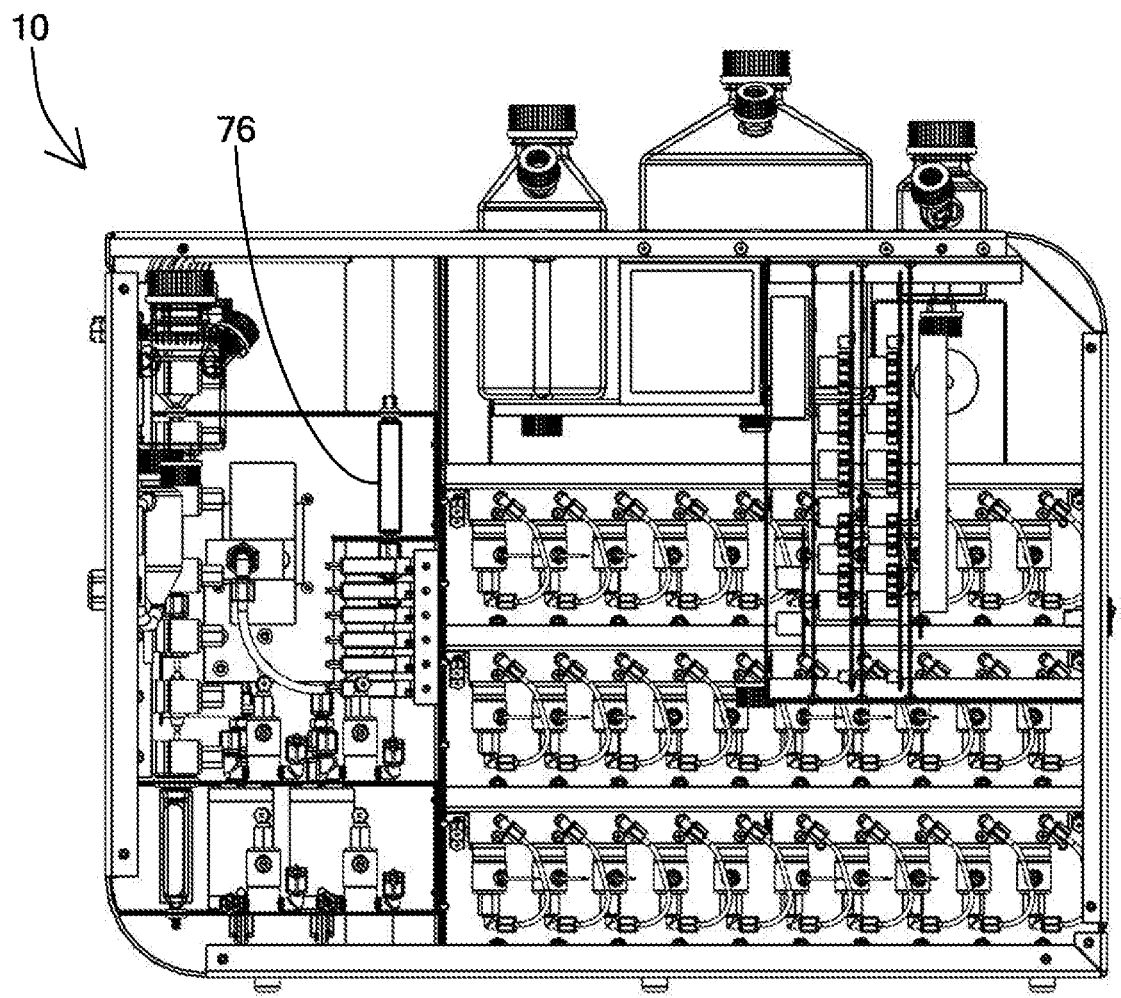
FIG. 11 illustrates a back view of the chemical synthesis instrument of FIG. 1 with the back housing removed.
Figure 12:
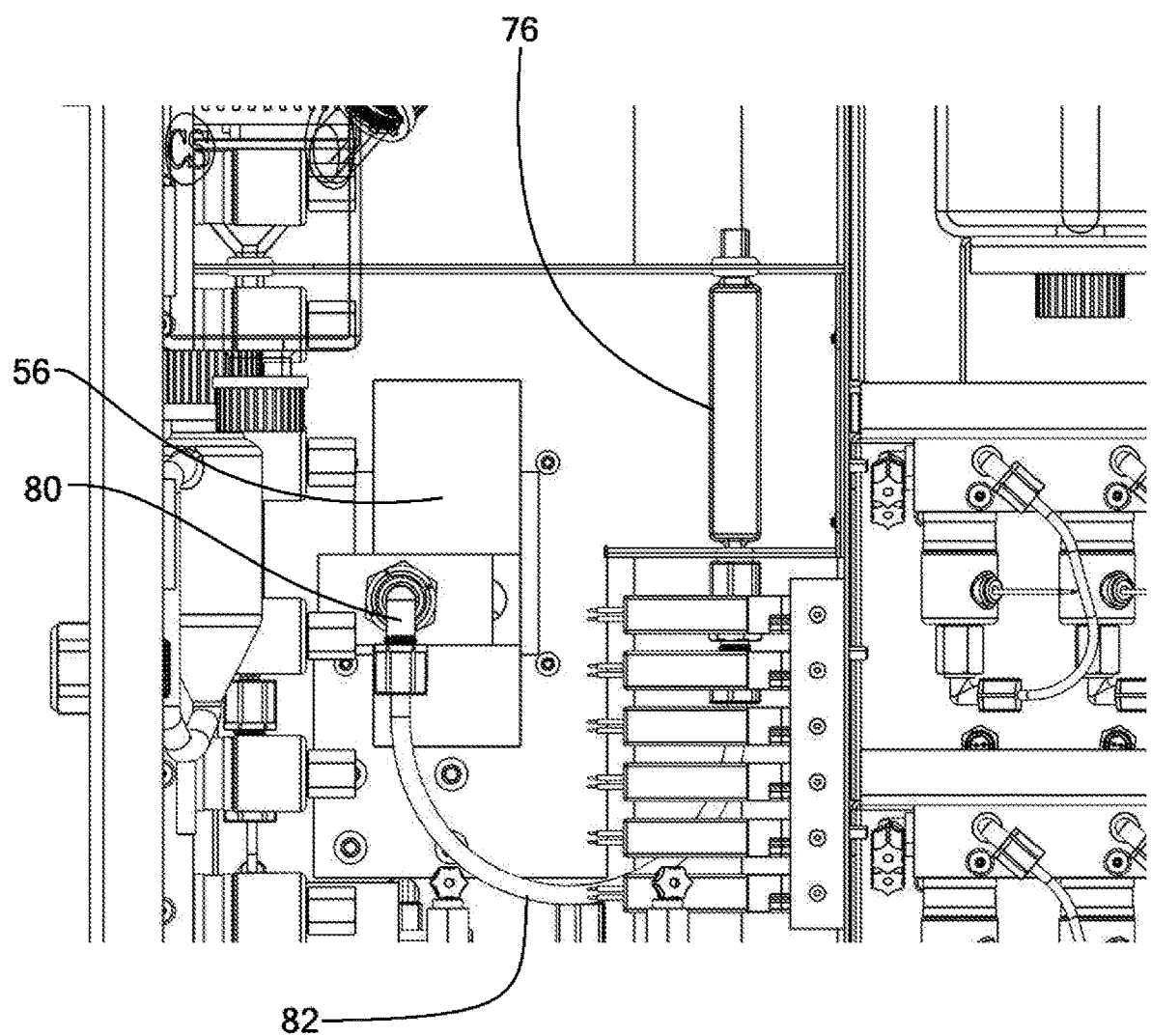
FIG. 12 illustrates a detailed back view of the chemical synthesis instrument of FIG. 1, highlighting the second chamber of the double reaction vessel system of FIG. 10.

Referring to FIGS. 10 through 12, a double reaction vessel system 60 is shown. There is a need for adequate mixing within the reaction vessel to ensure solvent to resin contact and result in chemical efficiency. Nitrogen bubbling is a typical method of mixing, as no mechanical movement is required to perform this mixing. However, in every reaction vessel, filters are needed at the top and the bottom to hold the resin inside the reaction vessel chamber (the interior region 30 of reaction vessel 20, as discussed above with respect to FIG. 4, for example), while allowing solvents and reaction solutions to be transferred in and out.

When bubbling with nitrogen, more vigorously bubbling is required to ensure good mixing. However, more vigorous bubbling can push solvent out of the reaction vessel, through the filter, and into the waste. Another problem with conventional systems is that, when bubbling with nitrogen, the resin can stick on the top portion of the reaction vessel, thus reducing solvent to resin contact with that stuck resin.

The double reaction vessel system 60 can include a first chamber 62, which can be the reaction vessel for peptide synthesis. In some embodiments, the first chamber 62 can be reaction chamber 20, as described above. A valve mechanism 64 can permit nitrogen flow 66 to enter the first chamber 62, can permit waste 68 to exit the first chamber 62 and can permit solvent and/or reagents 70 to enter the first chamber 62.

The upper end 72 of the first chamber 62 can connect to a lower end 74 of a second chamber 76. When vigorous bubbling is provided in the first chamber 62, any solvent pushed out can be collected in the second chamber 76. This overflow solvent can be pushed back into the first chamber 62 (the reaction vessel) via a nitrogen pressure 78, for example. This can both 1) replace the overflow solvent/reagent, and 2) un-stick any resin that may be stuck to the top of the first chamber 62 due to the vigorous bubbling.

Figure 9:
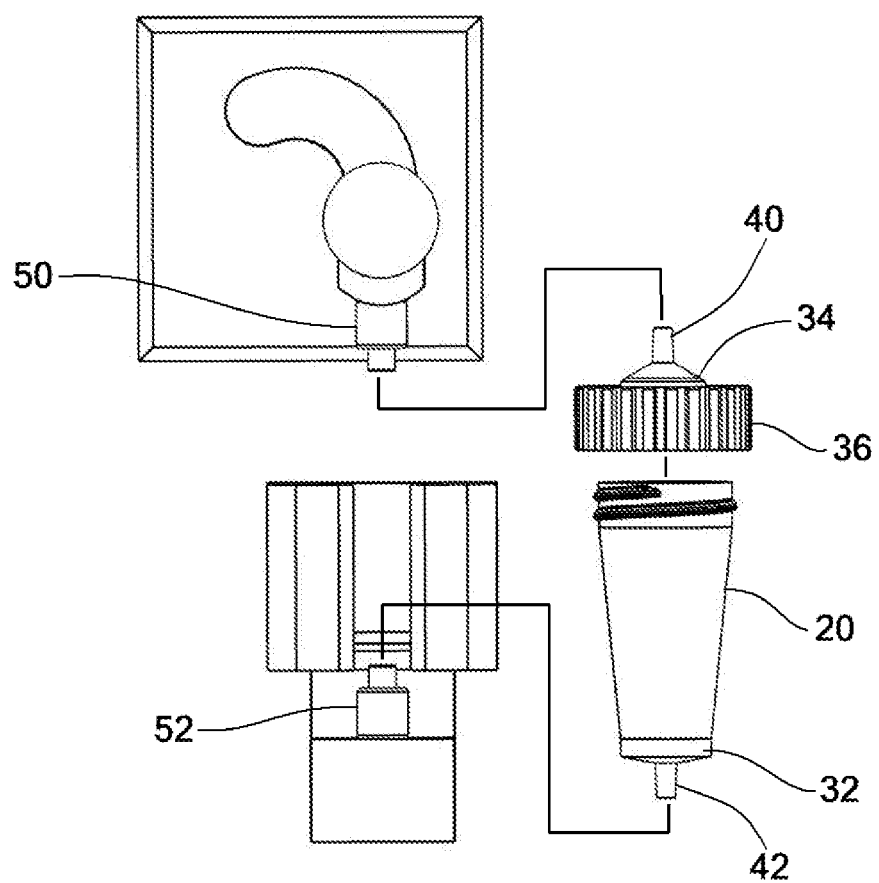
FIG. 9 illustrates a partially exploded view of the reaction vessel removed from the double action compression reaction vessel connection mechanism of FIG. 5.

Referring to FIGS. 11 and 12, the double reaction vessel system 60 is shown installed in instrument 10 from a back view with a portion of the housing removed for clarity. A connector 80 may pass lines through the housing to permit connection with the upper end 72 of the first chamber 62. Connection tubes 82 may be used to connect to the lower end 74 of the second chamber 76. Additional valving and tubing, as illustrated in FIG. 9, is not shown in FIGS. 10 and 11 for clarity.

Figure 13:
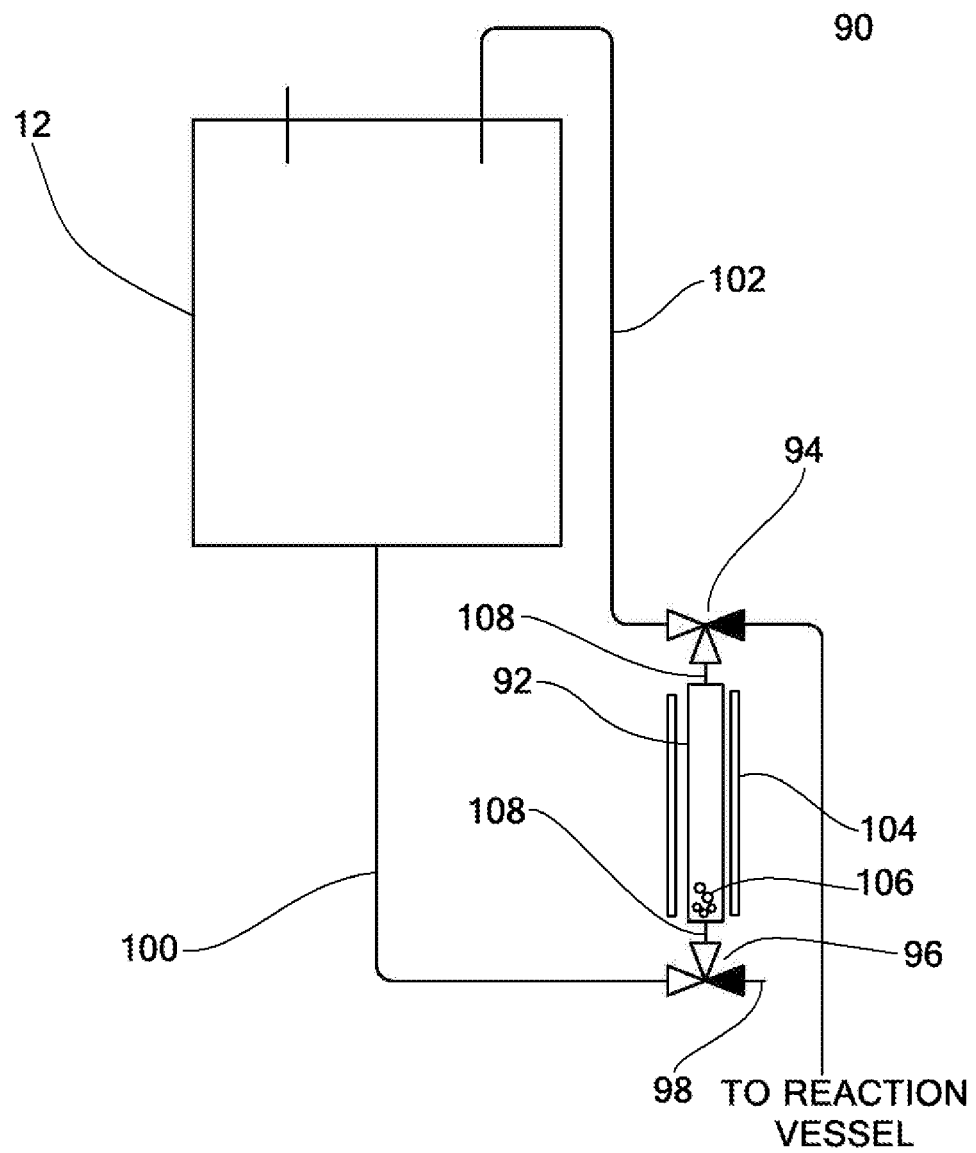
FIG. 13 illustrates a gravity fed reservoir for solvent delivery usable in the chemical synthesis instrument of FIG. 1.

Referring to FIG. 13, a gravity fed reservoir system 90 is shown. Solvent delivery to the reaction vessel needs to be measured to a specific amount and then delivered to the reaction vessel. This can be performed in various ways that involve pumps, sensors for measurement, calibrated timed delivery and gas pressure.

According to aspects of the present invention, the gravity fed reservoir system 90 can use gravity fed reservoirs 92 with valves 94, 96 that establish the fixed volume for delivery. The gravity fed reservoir 92 can have an inlet 108 on the top and bottom connected to the valves 94, 96, typically three-way valves, as illustrated. The bottom valve 96 can be connected to nitrogen pressure 98 and a solvent reservoir (such as solvent bottle 12) via line 100. The normal path for the valve 96 is to allow the solvent reservoir to fill the gravity fed reservoir 92, where the normal path for the valve 94 is to permit the solvent to fill the reservoir 92 and extend out through line 102 back toward the bottle 12.

To deliver the solvent from the gravity fed reservoir 92 to the reaction vessel, the valve 96 is opened and nitrogen pressure 98 is delivered, pushing the fixed volume between the two valves 94, 96, where the valve 94 can open to permit the fixed volume to be delivered to the reaction vessel. Upon release, both valves 94, 96 are returned to their normal position, as described above, to permit the solvent reservoir to refill the loop and the gravity fed reservoir 92.

In some embodiments, the solvent fed reservoir 92 can be enclosed in a heating mechanism 104 to permit pre-heated solvent to be delivered to the reaction vessel. The heating mechanism 104 can be, for example, an enclosed block with a heading cartridge, induction heating via an induction coil with a metal gravity fed reservoir, induction heating with metal balls 106 disposed in the gravity fed reservoir 92, or the like. In some embodiments, a quantity of metal balls within the gravity fed reservoir 92 can be used to control the volume of solvent delivered to the reaction vessel.

Figure 14:
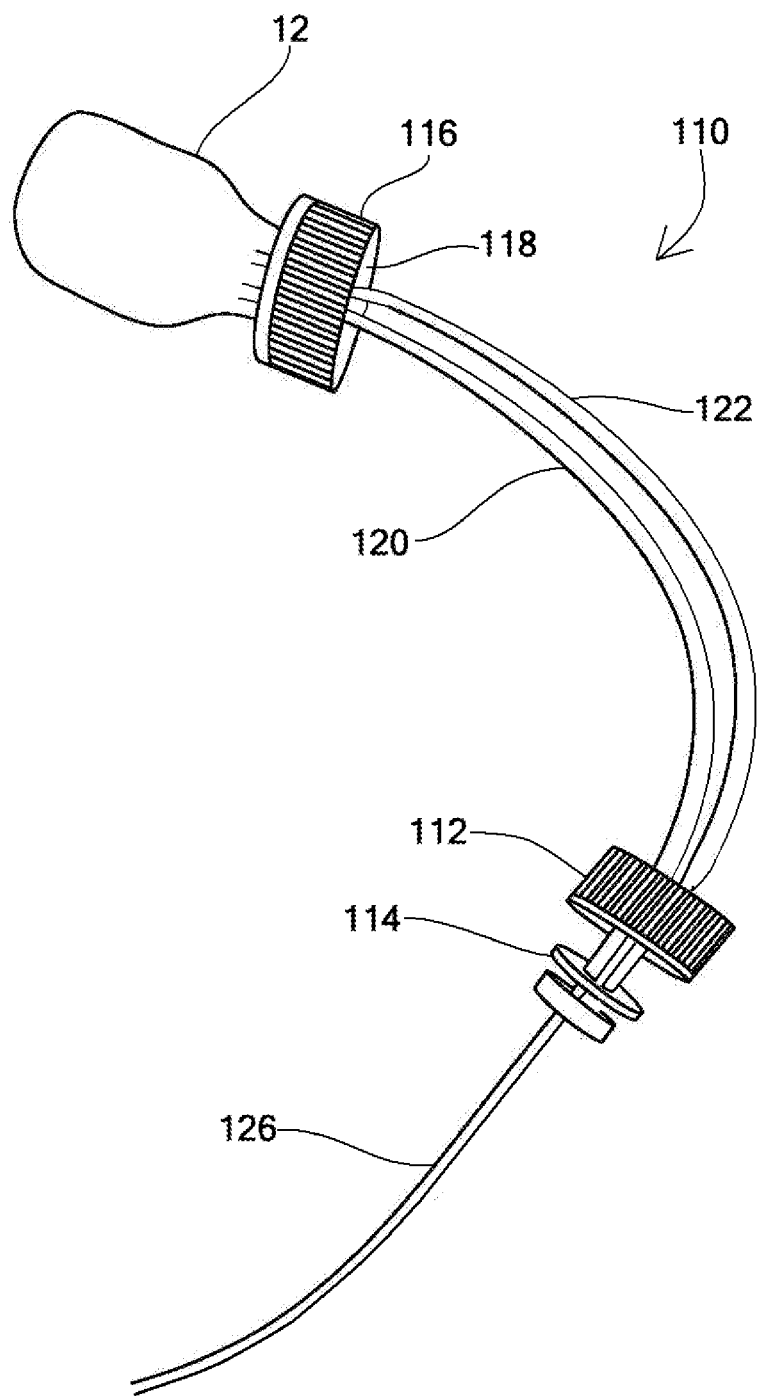
FIG. 14 illustrates a fume-free solvent refill connection usable in the chemical synthesis instrument of FIG. 1.
Figure 15:
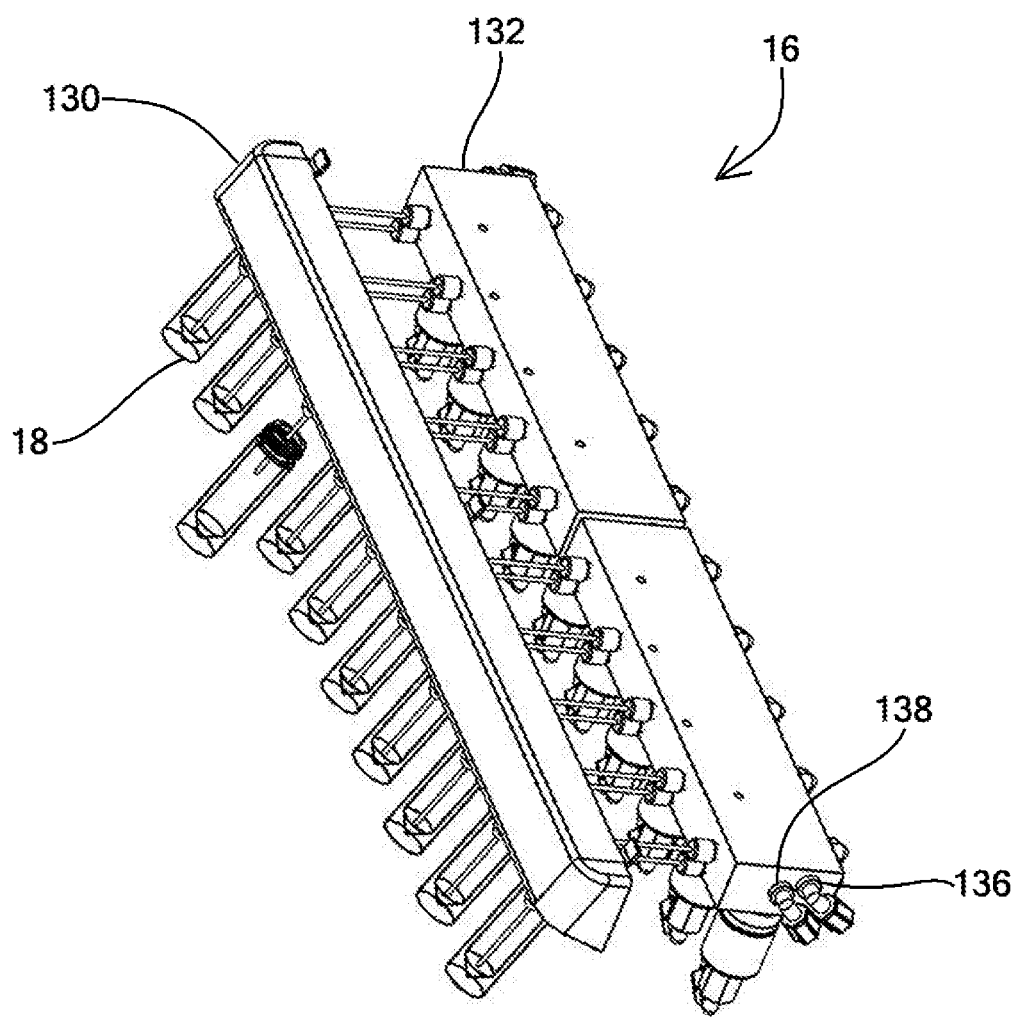
FIG. 15 illustrates a top perspective view of a manifold assembly usable in the chemical synthesis instrument of FIG. 1.
Figure 16:
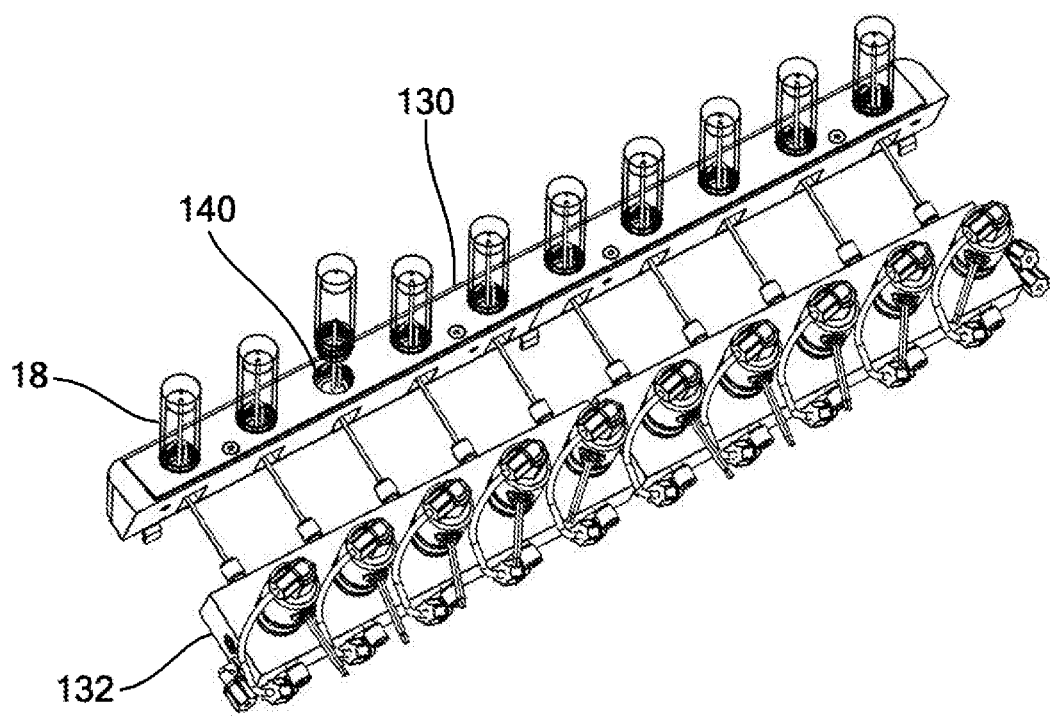
FIG. 16 illustrates a bottom perspective view of the manifold assembly of FIG. 15.
Figure 17:
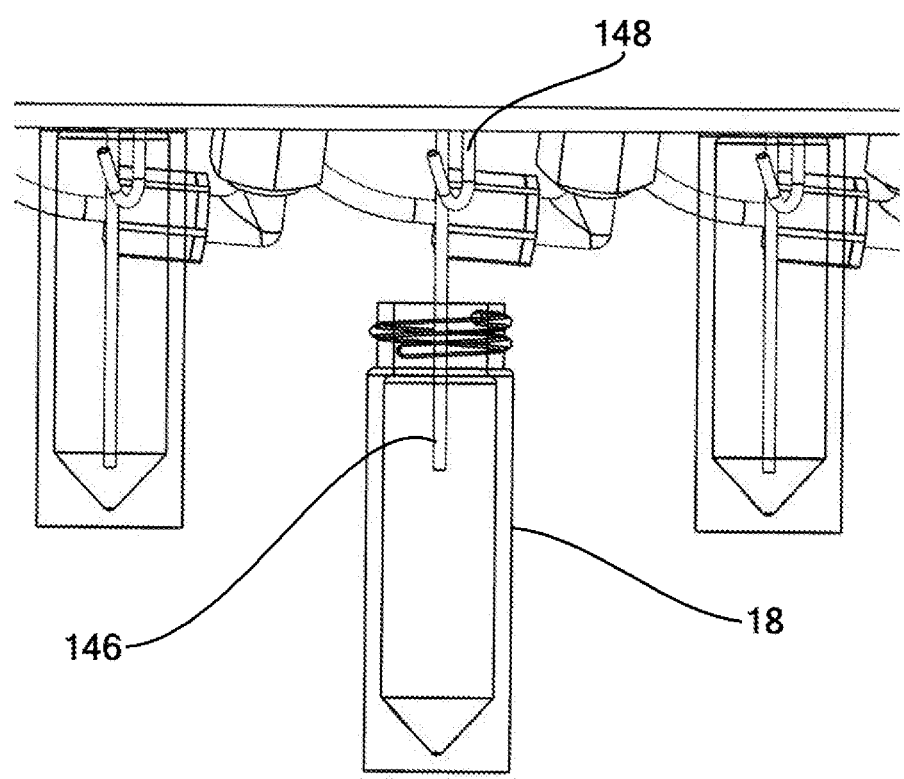
FIG. 17 illustrates a detailed front view of a vial disassembled from the manifold assembly of FIG. 15.
Figure 18:
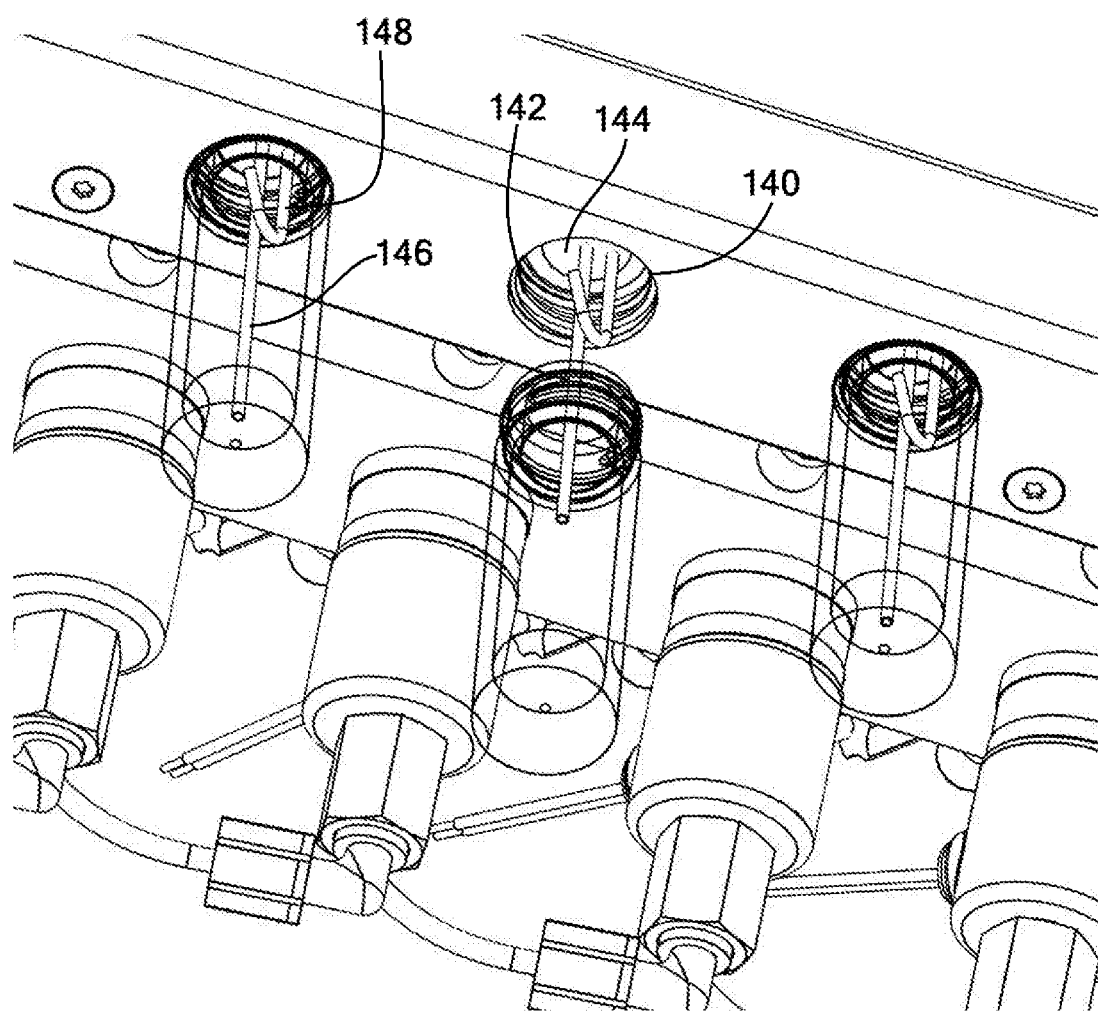
FIG. 18 illustrates a detailed view of the threaded connection for connecting vials to the manifold assembly of FIG. 15.
Figure 19:
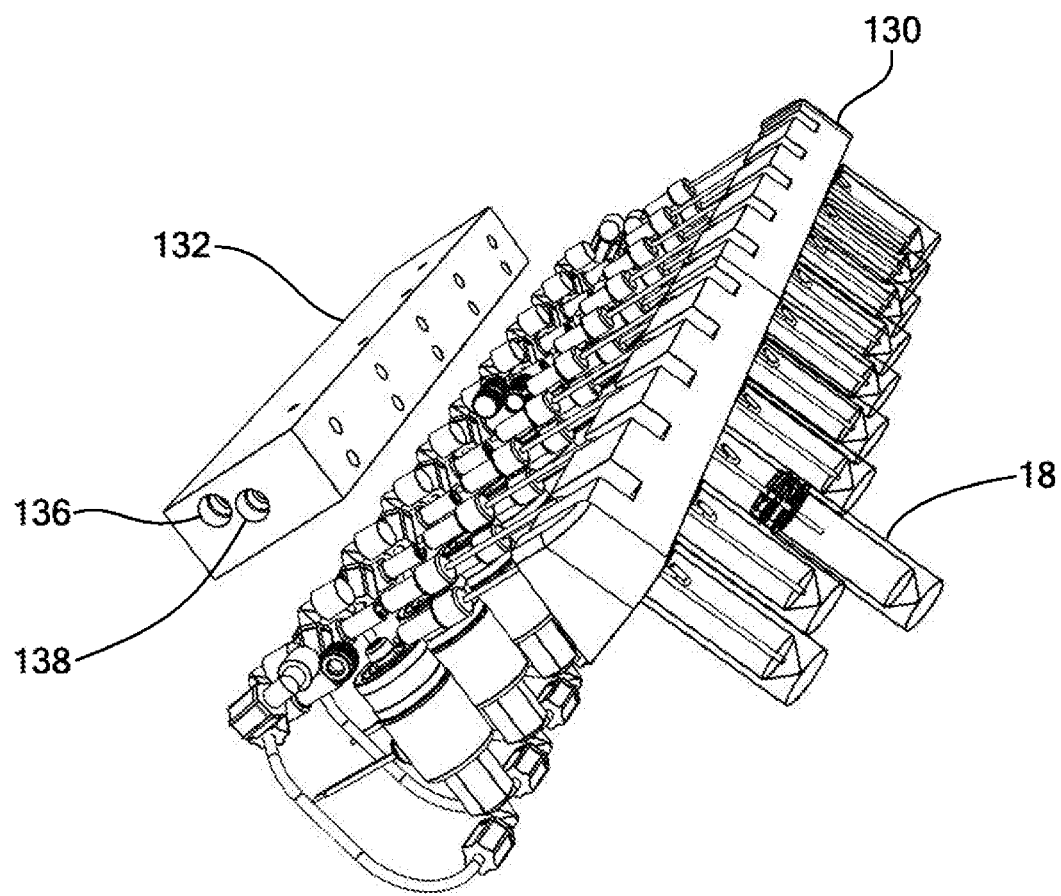
FIG. 19 illustrates a partially exploded view of the manifold assembly of FIG. 15, illustrating a block of the second manifold removed therefrom, and a cover of the first manifold removed therefrom.

Referring to FIGS. 1 and 14, as discussed above, the solvent bottles 12 may be held in place with a gasket 22 that prevents rotation of the solvent bottle 12 when the cap 26 is turned. Conventional peptide synthesizers have solvent bottles that are used to feed the system to perform peptide synthesis. To refill the bottles, the user can unscrew the bottle, bring the bottle to a fume hood, and refill the bottle in the fume hood. Optionally, a user can unscrew the bottle and use a funnel to pour the solvent directly in place where the peptide synthesizer is located. Solvents used in peptide synthesis, such as piperidine, can be odorous and a lacrimator.

According to aspects of the present invention, with the solvent bottles 12 fixed in place, the cap 26 can be removed single-handedly by a user and a fume-free solvent addition accessory 110 can be used to safely and easily transfer solvent into the solvent bottles 12. The accessory 110 can include a cap 116 that matches the cap 26 of the solvent bottles 12. The cap 116 can include an insert 118 with two holes. First tubing 120 and second tubing 122 can extend from the cap 116 to a second cap 112 with an insert 114, similar to insert 118, with two holes. The tubing 120, 122 can extend through the holes in the inserts 114, 118. The cap 112 can connect to a refill bottle.

The first tubing 120 can extend a length 126 beyond the insert 114 to go into the refill bottle and to be present in an air space in the refill bottle when the refill bottle is turned upside down to refill the solvent bottle 12. The second tubing 122 can extend only slightly past the insert 114 to provide solvent flow out of the refill bottle. First tubing 120 and second tubing 122, at the solvent bottle 12, can extend just into the insert 118 on the cap 116. Thus, refill solvent can pass from the refill bottle via second tubing 122 and a venting flow can move from the solvent bottle 12 being refilled, back into the refill bottle via first tubing 120. In some embodiments, the tubing 120, 122 may extend beyond a predetermined distance from the insert 118 to provide a limit on the amount of solvent that can be transferred into the solvent bottle 12. The solvent bottle 12 is shown away from the instrument 10, but it should be understood that refilling can occur at the instrument 10, without fear of spillage or solvent fume release.

Referring to FIGS. 15 through 19, an amino acid manifold 16 is shown. Currently, individual bottles, individual gaskets, individual caps and individual inserts, with the respective lines to an individual valve, with its respective individual fittings and tubing, are used to deliver solvent from that bottle to another reservoir.

According to aspects of the present invention, a manifold 16, also referred to as a manifold assembly 16, can include a first manifold 130 and a second manifold 132. The first manifold 130 can include a plurality of ports 140 with threaded counter bores 142 that allow vials 18 to screw directly into the first manifold 130. The threaded counter bore 142 can include a conical feature 144 that seals the vial 18 to the interface without the need for a gasket. Two lines 146, 148 can extend through conical feature 144 to enter the vial 18. One line 146 is configured for moving solution from the vial 18. The other line 148 provides venting/an inert gas to the vial 18. The first manifold 130 permits the vials 18 to be attached thereto with a single hand while not requiring any additional support.

The second manifold 132 allows for all the valves 134 to be screwed into a single manifold assembly. The second manifold 132 directs the flow of fluidics for the first manifold 130. The second manifold 132 can include a fluid flow channel 138 and a vent/inert gas channel 136. In operation, the appropriate valve 134 can actuate to remove a portion of the contents of a vial 18 into the fluid flow channel 138 and such fluid can be delivered to the reaction chamber, as appropriate. The vent/inert gas channel 136 can be connected, for example, to a nitrogen gas source to provide inert gas supply to each vial as contents are removed therefrom.

A plurality of manifold assemblies 16 can be used in the instrument 10. As shown in FIG. 1, in one embodiment, three manifold assemblies 16 can be used, providing for the use of up to thirty different amino acid reagents.

All the features disclosed in this specification, including any accompanying abstract and drawings, may be replaced by alternative features serving the same, equivalent or similar purpose, unless expressly stated otherwise. Thus, unless expressly stated otherwise, each feature disclosed is one example only of a generic series of equivalent or similar features.

Claim elements and steps herein may have been numbered and/or lettered solely as an aid in readability and understanding. Any such numbering and lettering in itself is not intended to and should not be taken to indicate the ordering of elements and/or steps in the claims.

Many alterations and modifications may be made by those having ordinary skill in the art without departing from the spirit and scope of the invention. Therefore, it must be understood that the illustrated embodiments have been set forth only for the purposes of examples and that they should not be taken as limiting the invention as defined by the following claims. For example, notwithstanding the fact that the elements of a claim are set forth below in a certain combination, it must be expressly understood that the invention includes other combinations of fewer, more or different ones of the disclosed elements.

The words used in this specification to describe the invention and its various embodiments are to be understood not only in the sense of their commonly defined meanings, but to include by special definition in this specification the generic structure, material or acts of which they represent a single species.

The definitions of the words or elements of the following claims are, therefore, defined in this specification to not only include the combination of elements which are literally set forth. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptually equivalent, what can be obviously substituted and also what incorporates the essential idea of the invention.

What is claimed is:

1. A chemical synthesis device comprising:
   a reaction vessel;
   a lower connector configured to provide sealed engagement to a lower tapered fitting of the reaction vessel;
   an upper connector configured to provide sealed engagement to an upper tapered fitting of the reaction vessel;
   a knob attached to the upper connector;
   an upper connector path formed in a housing of the chemical synthesis device, the upper connector path permitting movement of the knob and upper connector upward to disconnect the upper connector from the upper tapered fitting, and downward to a reaction vessel connection position where the upper connector engages with the upper tapered fitting of the reaction vessel; and
   a force application mechanism to provide a downward force to the upper connector, urging the upper connector to the reaction vessel connection position, wherein the force application mechanism is a weight disposed inside the housing.

2. The chemical synthesis device of claim 1, wherein the lower connector is movable downward against a resilient force.

3. The chemical synthesis device of claim 2, wherein the resilient force is provided by one or more springs.

4. The chemical synthesis device of claim 1, wherein the upper connector path includes a vertical component, permitting the upper connector to engage to and disengage from the upper tapered fitting, and a horizontal component, permitting the upper connector to be maintained in a non-engagement position with the upper connector disengaged from the upper tapered fitting.

5. The chemical synthesis device of claim 1, further comprising a heating element configured to provide heat to one or more reaction vessel holding arms.

6. The chemical synthesis device of claim 1, wherein the reaction vessel comprises:
   a hollow tubular body;
   a first filter disposed at a first end of the hollow tubular body;
   a cap removably fitting on a second end of the hollow tubular body; and
   a second filter disposed in the cap, where an interior region is defined between the first filter and the second filter when the cap is attached on the second end of the hollow tubular body, wherein
   the lower tapered fitting is fitted on the first end of the hollow tubular body providing fluid communication from outside the reaction vessel to the interior region; and
   the upper tapered fitting is fitted on the cap providing fluid communication from outside the reaction vessel to the interior region.

7. The chemical synthesis device of claim 6, wherein the hollow tubular body has a uniform cross-section along a length thereof.

8. The chemical synthesis device of claim 6, wherein the hollow tubular body has an increasing cross-sectional diameter from the first end to the second end.

9. A chemical synthesis device, comprising:
   a double reaction vessel system comprising:
      a first reaction chamber having fittings at an upper end and a lower end thereof, the first reaction chamber comprising:
         a hollow tubular body;
         a first filter disposed at a first end of the hollow tubular body;
         a removable cap attachable on a second end of the hollow tubular body; and
         a second filter disposed in the cap, where an interior region is defined between the first filter and the second filter when the cap is attached on the second end of the hollow tubular body;
         wherein the fittings include:
            a first fitting on the first end of the hollow tubular body providing fluid communication from outside the first reaction chamber to the interior region; and
            a second fitting on the cap providing fluid communication from outside the first reaction chamber to the interior region;
      a second chamber fluidly connected at its lower end to the upper end of the first reaction chamber;
      a waste connection at an upper end of the second chamber;
      a first inert gas connection at the upper end of the second chamber, the first inert gas connection operable to provide an inert gas flow through the second chamber, from the upper end to the lower end, and into the first reaction chamber; and
      a second inert gas connection operable to provide an inert gas into the first reaction chamber via the lower end thereof; and
   a reaction vessel installation and removal mechanism comprising:
      a lower connector configured to provide sealed engagement to the first fitting of the first reaction chamber;
      an upper connector configured to provide sealed engagement to the second fitting of the first reaction chamber;
      a knob attached to the upper connector;
      an upper connector path formed in a housing of the chemical synthesis device, the upper connector path permitting movement of the knob and upper connector upward to disconnect the upper connector from the second fitting, and downward to a reaction vessel connection position where the upper connector engages with the second fitting of the reaction vessel; and
      a force application mechanism to provide a downward force to the knob upper connector, urging the upper connector to the reaction vessel connection position, wherein the force application mechanism is a weight disposed inside the housing.

10. The chemical synthesis device of claim 9, wherein the hollow tubular body has a uniform cross-section along a length thereof.

11. The chemical synthesis device of claim 9, further comprising a solution flow connection at the lower end of the first reaction chamber operable to provide a solvent or a solution into the first reaction chamber.

12. The chemical synthesis device of claim 9, further comprising a solvent flow connection at the upper end of the second chamber providing a rinse solvent flow through the second chamber and the first reaction chamber.

13. The chemical synthesis device of claim 12, further comprising a waste flow connection at the lower end of the first reaction chamber operable to provide the rinse solvent to a waste container.

14. The chemical synthesis device of claim 9, further comprising one or more three-way valves operable to adjust a flow through at least one of the first reaction chamber and the second chamber.

15. A chemical synthesis device comprising:
a reaction vessel;
a lower connector configured to provide sealed engagement to a lower tapered fitting of the reaction vessel;
an upper connector configured to provide sealed engagement to an upper tapered fitting of the reaction vessel;
a knob attached to the upper connector; and
an upper connector path formed in a housing of the chemical synthesis device, the upper connector path permitting movement of the knob and upper connector upward to disconnect the upper connector from the upper tapered fitting, and downward to a reaction vessel connection position where the upper connector engages with the upper tapered fitting of the reaction vessel, wherein the upper connector path includes a vertical component, permitting the upper connector to engage to and disengage from the upper tapered fitting, and a horizontal component, permitting the upper connector to be maintained in a non-engagement position with the upper connector disengaged from the upper tapered fitting.

16. The chemical synthesis device of claim 15, wherein the lower connector is movable downward against a resilient force.

17. The chemical synthesis device of claim 16, wherein the resilient force is provided by one or more springs.

18. The chemical synthesis device of claim 15, further comprising a force application mechanism to provide a downward force to the upper connector, urging the upper connector to the reaction vessel connection position.

19. The chemical synthesis device of claim 18, wherein the force application mechanism is a weight disposed inside the housing.

* * * * *